US005409893A

United States Patent [19]

Alessio et al.

[11] Patent Number: 5,409,893

[45] Date of Patent: Apr. 25, 1995

[54] RUTHENIUM(III) COMPLEXES AS ANTINEOPLASTIC AGENTS

[75] Inventors: Enzo Alessio; Giovanni Mestroni; Sabrina Pocar; Gianni Sava; Silvano Spinelli, all of Milan, Italy

[73] Assignee: Boehringer Mannheim Italia, S.p.A., Milan, Italy

[21] Appl. No.: 773,939

[22] PCT Filed: May 2, 1990

[86] PCT No.: PCT/EP90/00699

§ 371 Date: Dec. 13, 1991

§ 102(e) Date: Dec. 13, 1991

[87] PCT Pub. No.: WO90/13553

PCT Pub. Date: Nov. 15, 1990

[30] Foreign Application Priority Data

May 5, 1989 [IT] Italy .................................. 20385/89

[51] Int. Cl.[6] .................. A61K 31/41; A61K 31/535; C07F 15/00

[52] U.S. Cl. .......................................... 514/6; 546/4; 549/3

[58] Field of Search ..................... 546/4; 549/3; 514/6

[56] References Cited

U.S. PATENT DOCUMENTS 3,557,143 1/1971 Suh et al. ................................ 549/3

3,576,012 4/1971 Matlack ................................. 549/3

OTHER PUBLICATIONS

Sarma et al. Polyhedron, 7, No. 18, pp. 1727–1735, 1988.

Metal Complexes in Cancer Therapy, "The Development of Tumor-Inhibiting Ruthenium Dimethylsulfoxide Complexes", pp. 161–187, 1993.

*Primary Examiner*—Mukund J. Shah
*Assistant Examiner*—P. K. Sripada
*Attorney, Agent, or Firm*—Nikaido, Marmelstein, Murray & Oram

[57] ABSTRACT

The invention concerns a coordination complexes with $R^{111}$ as central metal attached to a heterocyclic ligand in the apical position trans to a sulfoxide and their pharmaceutical compositions useful in antitumor therapy either alone or in combination with platinum complexes.

10 Claims, No Drawings

RUTHENIUM(III) COMPLEXES AS ANTINEOPLASTIC AGENTS

The present invention relates to octahedric ruthenium(III) complexes, to a process for their preparation and to pharmaceutical compositions containing them.

After the discovery of the antineoplastic properties of cis-diamino dichloro-platinum(II) (cisplatin), the interest for metal organic complexes as potential anti-tumor agents increased (see for instance M. J. Cleare et al., "Antitumor properties of metal complexes"; Sigel H. (ed.) "Metal ions in biological system (Vol. II ) metal complexes as anticancer agents". M.Dekker, Inc. Basel, N.Y. (pages 1–56)

Cisplatin is now widely used in anti-tumor mono-or polychemotherapy (see for example A. W. Prestayko et al., Cisplatin: current status and new developments, Acad. Press Inc., New York, 1980), and similarly to several anti-tumor agents its spectrum of action covers some kinds of tumor (testis, ovary, bladder, head-neck). Other tumors, such as disseminated lungs or breast tumors or the colon-rectal tumor are not sensitive to treatment with this compound (see for example Osieka R. et al., Klin. Wochenschr. 57, 1249 (1979).

The search of new metal-organic complexes is aimed at the development of new compounds (containing Pt and/or other transition elements) endowed with a wider spectrum of activity and lower toxicity than known anti-tumor agents. The use of ruthenium as an alternative to platinum was first suggested by L. J. Anghileri et al., (Krebsforsch. 83, 213, 1975) with studies on "Ruthenium Rot" or ruthenium polycations provided with anti-tumor activity. The anti-tumor activity of Ruthenium(II) or (III) complexes has been already disclosed by T. Giraldi et al., (Cancer Res. 37, 2662, 1977); M. J. Clarke (Acs. Symp. Ser. 149, 157, 1980).

The synthesis of Ru(II) anionic complexes with 5-membered heterocycles, such as imidazole and pyrazole was described by F. Kralik (Collec. Czecho. Chem Comm., 26, 1298, 1961); S. A. Zaichi (Transition Metalchemie, Vol. 4, No. 2, Verlag Chemie, pag. 133–136) prepared imidazole complexes and subsequently Ru(II) and Ru(III) complexes were synthetized by J. Levis (J. Chem. Soc. (A) 366–370, 1967).

The anti-tumor activity of some of these complexes has been studied; particular attention was paid to imidazolium bis-imidazole-tetrachloro ruthenate(III) (ICR) whose activity was studied in classic experimental tumors such as P388 leukemia and/or B16 melanoma (B. K. Keppler et al., J. Cancer Res. Oncol., 111, 166 (1986) and against an autoctone colon-rectal tumor induced by acetoxymethyl methylnitrosamine (F. T. Garzon et al., Cancer Chemoter. Pharmacol., 19, 347, 1987). Neutral complexes of Ru(III) of formula $B_3$ $RuX_3$ wherein B is a basic heterocycle (mono or polycyclic) containing one or more nitrogen atoms and X is chlorine or bromine, having anti-tumor activity are described in WO 86/00804 as well as co-precipitates thereof with polyvinylpyrrolidone of MW=1700, suited to overcome their poor water solubility, allowing the preparation of aqueous solutions useful for administration to animals.

Trans complexes of Ru (II), a namely trans-Ru(II)-tetrakisdimethylsulphoxide, are reported by G. Mestroni et al. (Italian Pat. Appln. 20180 A/87) as endowed, at equitoxic dosages, with a cytotoxic activity at least 10 times higher than that of the above cited complexes cis-Ru(II)-tetrakis-dimethylsulphoxide (T. Giraldi et al., above cited).

We have found that the contemporary presence of sulphoxide and basic nitrogen ligands in the apex positions of the octahedric neutral and anionic ruthenium (III) complexes produces compounds endowed with considerable anti-tumour activity.

The complexes of the invention have the following formula (I):

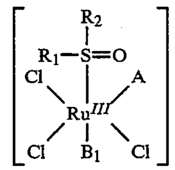

(I)

wherein $R_1$ and $R_2$, which are the same or different, are $C_1$–$C_6$-alkyl, $C_3$–$C_7$-cycloalkyl, $C_3$–$C_7$ cycloalkyl-($C_1$–$C_6$)-alkyl, phenyl, aryl-($C_1$–$C_6$)-alkyl, a 5- or 6-membered heterocyclic group containing at least one oxygen or nitrogen atom, a heterocyclyl-($C_1$–$C_6$)-alkyl group wherein the heterocycle residue is as above defined, or $R_1$ and $R_2$ together with the sulphur atom to which they are bound form a ring of formula

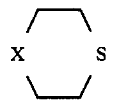

wherein X is a bond, oxygen or a $-(CH_2)_m$ group, m=1 or 2,

A is a group

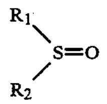

as above defined or chlorine;

—$B_1$ is a nitrogen ligand selected in the group of ammonia, a primary, secondary or tertiary amine or a nitrogen containing heterocyclic group.

When either $R_1$ or $R_2$ are phenyl, aryl-($C_1$–$C_6$)-alkyl, heterocyclic or heterocyclyl-($C_1$–$C_6$)-alkyl, they can be substituted by one or more ($C_1$–$C_4$) alkyl, methoxy, halogen, nitro, cyano, hydroxy, ($C_1$–$C_6$)-alkoxycarbonyl, trifluoromethyl groups.

When A is chlorine the complex has a negative charge that is then balanced by a non-toxic counter ion, preferably an alkaline or alkaline earth cation. The hydrates and solyates of the complexes of formula I are also included in the invention.

Primary, secondary or tertiary amines of group B may be represented by formula NRaRbRc wherein Ra, Rb and Rc, that can be the same or different, are hydrogen; $C_1$–$C_6$-alkyl optionally substituted by one or more hydroxy, $C_1$–$C_4$-alkoxy, $C_1$–$C_4$-alkylthio, $C_3$–$C_7$-cyctoalkyl, phenyl, phenoxy, benzyloxy, 4-histidyl, carboxy, $C_1$–$C_4$-alkoxycarbonyl; $C_3$–$C_7$-cycloalkyl; phenyl; the phenyl, phenoxy or benzyloxy groups may optionally be substituted by one or more hydroxy or $C_1$–$C_6$ alkyl groups.

When $B_1$ represents a nitrogen containing heterocyclic group, it is a 5- to 7-membered ring which is aromatic, saturated or partially saturated, containing at least one nitrogen atom, having its electronic doublet involved in the bond with the ruthenium atom and optionally other oxygen, sulphur and/or nitrogen atoms, the latter optionally substituted by $C_1$–$C_4$-alkyl, benzyl or phenyl, optionally benzo-fused and optionally substituted by one or more $C_1$–$C_6$-alkyl, $C_1$–$C_4$-alkoxy, $C_1$–$C_4$-alkylthio or phenyl, the phenyl groups possibly substituted by one or more hydroxy, $C_1$–$C_4$-alkoxy, $C_1$–$C_6$-alkyl, nitro, cyano, halogen, trifluoromethyl, $C_1$–$C_4$-alkoxycarbonyl groups. When A is a sulphoxide group the metal atom is an asymmetric center and consequently the compounds I are racemates.

When another asymmetrical center is present in both $B_1$ and/or in sulphoxide groups, the compounds I will be diastereoisomers.

Of course the anionic complexes wherein A is the chloride ion will be diastereoisomers when either the ligand $B_1$ or the group

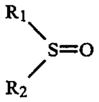

comprise asymmetrical centers.

The invention includes the complexes I in all possible steric forms (racemates, enantiomers, diastereisomers).

Preferred examples of achiral sulphoxides of formula

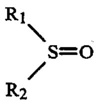

are: dimethylsulphoxide, diethylsulphoxide, dibenzylsulphoxide, diphenylsulphoxide, ditolylsulphoxide, tetramethylsulphoxide, pentamethylensulphoxide, dibutylsulphoxide.

Preferred examples of chiral sulphoxides are: methyl-ter-butylsulphoxide, methyl-p-tolylsulphoxide, methyl-2-chloro-phenylsulphoxide, methyl-4-chloro-phenylsulphoxide, methyl-3-chloro-phenylsulphoxide, methyl-4-fluoro phenylsulphoxide, ethyl-4-chloro-phenylsulphoxide, 4-chloro-phenyl-ter-butylsulphoxide.

Preferred examples of nitrogen ligands $B_1$ are ammonia, dimethylamine, diethylamine, ethylamine, triethylamine, ethanolamine, dimethylaminoethanol, diethylaminoethanol, trishydroxymethylaminomethane, 2-methylthiomethyl-amine, methionine methyl ester, methyl 3-methylthio-2-amino-propionate, ephedrine, cyclohexylamine, 1-phenyl-1-amino-ethane, 1-cyclohexyl-1-aminoethane, 2-amino-phenylethanol, 3-phenyl-2-amino-propane, N-methyl-3-phenyl-2-amino-propanol, methylglicinate, methyl N-methyl-glycinate, alanine methylester, phenylalanine methylester, histidine, N-methyl-N-(histidyl)-amine, morpholine, piperidine, N-methyl-morpholine, N-methyl-piperidine, N-benzylpiperidine, pyridine, imidazole, indazole, benzimidazole, 1-methyl-pyrrole, 1-benzylpyrrole, thia-zole, oxazole, 1-methylimidazole, 3,5-dimethylisoxazole, pyridine, pyrazole, 1-methylpyrazole, 1-benzyl-pyrazole, indole, 2-methylindole.

The complexes of formula I are prepared by a process comprising the reaction -of a nitrogen basic ligand $B_1$, as above defined,

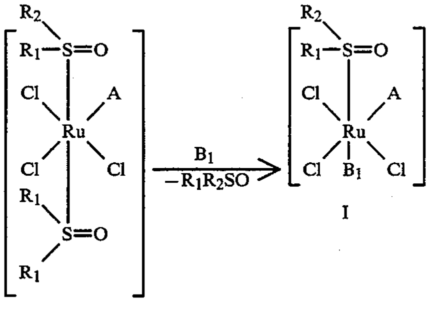

II I with a ruthenate(III) complex of formula II wherein $R_1$, $R_2$ and A are as above defined, in an inert solvent.

The ruthenates of formula II are synthetized starting from known sulphoxides and ruthenium trichloride.

Anionic trans-tetrachlororuthenates of formula IIa (A=Cl) are prepared by reaction, in inert solvents, of $RuCl_3$ hydrate with the desired sulphoxide of formula $R_1R_2SO$ in the presence of 37% aqueous HCl and, if desired, the proton counterion is exchanged with a sodium or potassium counterion by treatment with the corresponding alkaline chloride. Neutral trichlororuthenate(III) complexes of formula IIb ($A=R_1R_2SO$) are obtained by treating the complexes of formula IIa with $AgBF_4$ in the presence of an excess of the $R_1R_2SO$ sulphoxide in an inert solvent. Preferred inert solvents are alcohols (e.g. ethanol), halogenated hydrocarbons (e.g. $CHCl_3$), ketones (e.g. acetone), ethers (e.g. diethyl ether) or mixtures thereof.

The compounds of formula I are endowed with a remarkable anti-tumour activity as it has been proved in some pharmacological tests usings the model of Lewis lung carcinoma in rats.

For ex., tables I and II report some comparative results of experiments, with the compound of the ex. 1 and with both the ruthenate ICR and cis-DDP (cisplatin) used as reference drugs.

Comparative data on the effects of the tested substances on the growth of the primary rumor and on the survival time of treated animals are summarized in tables I and II.

TABLE I

Effects of treatment with compound of example 1 in comparison with trans-[R-(imidazole)2CL4] Imidazolium (ICR) and with cisplatin on growth of the primary tumor in animals affected by Lewis lung carcinoma

| Compound | Dosage* mg/kg/die | Evaluation period for primary tumor (mg/animal)** day 11 | day 18 | day 25 |
|---|---|---|---|---|
| controls | — | 953 143 | 6245 367 | 6133 637 |
| Compound | 100 | 530 72 | 2323 246 | 4523 247 |
| of ex. 1 | 120 | 500 80 | 1933 337 | 3017 585 |
| ICR | 40 | 790 119 | 2663 301 | 4612 479 |
| ICR | 48 | 542 71 | lethal | |
| cisplatin | 4 | 576 62 | 2581 220 | 5322 490 |

*Maximum dosages of compound of example 1 and ICR have a 1.2 increase of the relating equitoxic dosages.
**Average values E.S. of the individual values found in each group of treated animals.

The tumor is implanted subcutaneously on day 0 (0.05 ml tumor fragments per animal) and 24 h later the treatment is started, consisting of intraperitoneal injections on days 1, 5, 9, 13 after implantation. The weight of primary tumor is reported in the table, measured by means of a calliper and calculated on the bases of the formula: tumor weight $=a_2 \times b \times ( /6)$ wherein a and b represent two orthogonal diameters (a<b), and corresponds to days 11, 18 and 25 from tumor implant.

The treatment with compound of example 1 causes a larger weight reduction of the primary tumor than the one obtained with ICR and cisplatin at both dosages studied and on all days taken into consideration; the maximum reduction observed corresponds to a 51% weight reduction of the primary tumor in comparison with controls Maximum reductions observed with cisplatin amount to 40% (at early stage of growth) and to 25% with ICR ( terminal stage of growth).

The date further indicate that the compound of example 1 is provided with better therapeutic index than compound ICR, since a 20% increase of the dosage does not cause any lethal effect in the short time in the group of treated animals.

TABLE II

Effects of treatment with compound of example 1 in comparison with ICR and with cisplatin on survival time of treated animals

| Compound | Dosage** mg/kg/die | % of survived animals in days following surgery day 14 | day 22 | day 32 |
|---|---|---|---|---|
| controls | — | 67% | 33% | 11% |
| Compound of ex. 1 | 100 | 100% | 57% | 29% |
| ICR | 40 | 100% | 29% | 0% |
| cisplatin | 4 | 100% | 43% | 14% |

**Equitoxic dosages for the treatment schedule used.

The tumor is implanted intramuscularly on day 0 (0.05 ml of tumor fragments per animal ), on day 14 there is a surgical removal of the primary tumor (tumor mass average/animal=1.5 g) and after 24 h treatments consisting of intraperitoneal injections on days 1, 5, 9 and 13 following the surgery are started.

When ⅓ of the animals died for lung methastases, no difference was observed between the cisplatin treatment groups and the group treated with compound of example 1 and ICR, that are equally effective allowing survival of 100% of treated animals. By contrast, in more advanced phases, it is noticeable a major efficacy of compound of example 1 with respect to the reference compounds; in particular when ⅔ of the control animals died from methastases, in the group treated with compound of example 1 a 57% survival ratio is noticed, compared with 43% for cisplatin and 29% for ICR. This difference is even more evident when only 11% of control animals are alive (about 1 month after surgery); in this case the number of alive animals treated with compound of example 1 is twice with respect to that of cisplatin treated animals (29% vs. 14%); at this point all ICR treated animals were dead.

Similar results have been obtained with the compounds of the examples 2,3 and 4 when tested in comparison with cisplatin in the rat Lewis lung carcinoma model. All the compounds show % inhibition ranging from 54 to 78 at the 100 mg/kg/die dose level; at the effective dosages, the % of survived animals is also higher than that of animals treated with cisplatin.

It is remarkable that, as shown in table III, the coadministration of effective doses of the compounds of the invention of formula I with an effective dose of a platinum(II) complex, e.g. cisplatin, gives rise to increased cumulative effects on the reduction of the primary tumor observed for all the considered times and independently from the evaluation day.

TABLE III

Comparison of effects of treatment with compound of example 1 and cisplatin combined together with respect to the single compounds, on growth of primary tumor in rats affected by Lewis lung carcinoma

| Compound | Dosage mg/kg/die | Primary tumor (mg) evaluated after: day 11 av. | ES | % I | day 18 av. | ES | % I | day 25 av. | ES | % I |
|---|---|---|---|---|---|---|---|---|---|---|
| controls | — | 1175 | 195 | — | 3005 | 390 | — | 4051 | 478 | — |
| Cisplatin | 4 | 480 | 131 | 59 | 906 | 25 | 70 | 1036 | 179 | 74 |
| Compound of ex. 1 | 100 | 407 | 60 | 65 | 1103 | 248 | 63 | 1641 | 327 | 60 |
| Cisplatin + Compound of ex. 1 | 4 + 100 | 189 | 53 | 84 | 347 | 84 | 88 | 728 | 184 | 82 |

Variations of body weight at the end of the treatment: cisplatin −8.6%, compound of example 1—3.3%, cisplatin+compound of example 1—19.2%.

A synergistic effect of the ruthenate(III) complexes of the present invention with cis-platinum complexes, that could be inferred by the above experimental results, is novel; all the above experimental results evidence the remarkable activity of complexes of formula I with respect to the prior art compounds.

The complexes I can be administered to human patients in form of pharmaceutical compositions for treating various kinds of neoplasiae. The dosage of the complexes will depend on the kind of neoplasiae to be treated and on the conditions of the patient: in general the complexes will be administered at dosages ranging from about 10 mg to about 400 mg per $m^2$ of body surface per day. For a patient weighing 70 kg the dosage of active principle is ranging from 0.4 mg about to 1.600 mg per day.

This dosage regimen is of course selected individually in order to obtain an optimal therapeutical response.

For instance, the optimal dosage can be administered daily at subdivided doses, while the exact dosages depends obviously on age, weight and overall conditions of the patient.

The compounds (I) can be administered by intramuscular, subcutaneous or intraperitoneal route. The dosage can be administered at alternate days and/or for 2 consecutive days followed for 3 or more days without treatment.

The oral administration of the compounds of the invention is also possible, with doses at least 3–10 times higher than those by parenteral route.

The compounds of the invention can also be used in experimental protocols of polychemotherapy in combination with other anti-tumor compounds such as anthracyclines, cyclophosphamide, bleomycine, vinblastine, 5-fluorouracyl and particularly with cisplatin or its derivatives, in consideration of the surprising synergistic effects above reported.

The pharmaceutical compositions of the invention must be prepared using the normal care for the preparation of anti-tumor pharmaceutical compositions, using conventional diluents and excipients.

For example, for the administration of intravenous injections, sterile isotonic aqueous solutions or suspensions in aqueous or non aqueous medium are used, preferably prepared starting from conventionally prepared lyophilized active principles. The invention further includes compositions in form of combinations with platinum complexes, in particular cisplatin, for contemporary, sequential or separate use in cytostatic and anti-tumor therapy.

In the following examples, the compounds were characterized by elemental analysis, NMR, IR, UV and X-rays diffraction spectra.

Preparation 1

Synthesis of trans-[Ru(DMSO)$_2$Cl$_4$](DMSO)2H

At room temperature (r.t.), 37% aqueous HCl (1 ml) is added to a stirred solution of RuCl$_3$ hydrate (1.5 g) in DMSO (7 ml). The mixture is heated to 80° C. for 15 minutes and, after a further warming to 100° C. for 10 min, is cooled at r.t.

Dilution of the cooled orange solution with acetone (30 ml) and ethyl ether (Et$_2$O, 1 ml) affords the title compound (m.p. 120° C.), that is filtered, washed on filter with acetone/Et$_2$O (30:1) and dried under vacuum at r.t.

Preparation 2

Synthesis of trans-[Ru(DMSO)$_2$Cl$_4$]Na

A solution of NaCl (0.175 g, 3 mM) in water (0.5 ml) is added to a stirred solution of trans-[Ru(DMSO)$_2$Cl$_4$](DMSO)$_2$H (1.12 g; 2 mM) in EtOH (50 ml) and water (0.7 ml ). A microcrystalline precipitate of the title compound (m.p. 235° C.) is filtered, washed on filter with cold EtOH and dried.

Preparation 3

Synthesis of mer-[RuCl$_3$(DMSO)$_3$]

A solution of AgBF$_4$ (0.4 g; 2 mM) in acetone (15 ml) is added dropwise to a saturated solution of trans-[Ru(DMSO)$_2$Cl$_4$](DMSO)$_2$H in a stirred mixture of acetone (70 ml) and DMSO (0.5 ml), maintained at the reflux temperature. The reaction mixture is cooled at r.t. and the AgCl precipitate is removed by filtration. The filtrate is concentrated to 1/10 of the initial volume under vacuum to yield a crystalline precipitate of the title compound by dilution with Et$_2$O (1 ml) and cooling at 4° C. The product is filtered, washed with acetone/Et$_2$O and dried.

Preparation 4

Synthesis of trans-[RuCl$_4$(TMSO)$_2$](TMSO)H

A solution of 1 g of RuCl$_3$ hydrate in 30 ml absolute ethanol is refluxed for 3 hours to give a green solution that is filtered on paper and concentrated to small volume (3 ml).

The stirred solution is heated to 80° C. and treated with 1 ml of 37% aqueous HCl and 2 ml of freshly distilled tetramethylenesulphoxide (TMSO). The temperature is maintained for 10' at 80° C. (during this time the solution colour becomes red-orange).

By addition of acetone (10 ml) to the cooled mixture, the product precipitates in form of orange crystals. The crystals formation is facilitated by adding a few drops of ethyl ether. The crystals are filtered, washed with cold acetone and ethyl ether and then dried under vacuum at room temperature (75% yield).

Preparation 5

Synthesis of trans-Ru[(TMSO)$_2$Cl$_4$]Na

A solution of NaCl (0.175 g; 3 mM) in water (0.5 ml) is added to a solution of trans-[Ru(TMSO)$_2$Cl$_4$](TMSO)H (1.12 g, 2 mM) in a mixture of EtOH (50 ml) and water (0.7 ml) An immediate formation of the title compound, m.p. 238° C., occurs in the form of orange microcrystals that after collection by filtration are washed on filter with cold EtOH and dried.

The substitution in this procedure of the NaCl with the KCl yields the trans-[Ru(TMSO)$_2$Cl$_4$]K complex.

Using a sulphoxide selected from (R,S)-methyltolylsulphoxide, (S)-methyltolylsulphoxide, (R)methyltolylsulphoxide, the following complexes are also prepared:

trans-[Ru[(R,S)-methyltolylsulphoxide]$_2$Cl$_4$](R,S-methyltolylsulphoxide)H trans-[Ru[(R)-methyltolylsulphoxide]$_2$Cl$_4$](R-methyltolylsulphoxide)H trans-[Ru[(S)-methyltolylsulphoxide]$_2$Cl$_4$](S-methyltolylsulphoxide)H Preparation 6

Synthesis of mer-[RuCl$_3$(TMSO)$_3$]

A solution of AgBF$_4$ (0.4 g; 2 mM ) in acetone (15 ml) is added dropwise to a saturated soluzion of trans-[Ru(TMSO)$_2$Cl$_1$](TMSO)H in a stirred mixture of acetone (70 ml) and tetramethylenesulphoxide (TMSO, 0.5 ml), maintained at the reflux temperature. The reaction mixture is cooled at r.t. and the AgCl precipitate is removed by filtration. The filtrate is concentrated under vacuum to 1/10 of the initial volume and diluted with Et$_2$O (1 ml) to give by cooling at 0° C. a crystalline precipitate of the title compound (m.p. 140° C.) that filtered, washed on filter with cold acetone and dried.

In similar way, the following compounds are prepared:

mer-[RuCl$_2$(R,S-methyltolylsulphoxide)$_3$]

mer-[RuCl$_2$(R-methyltolylsulphoxide)$_3$]

mer-[RuCl$_2$(S-methyltolylsulphoxide)$_3$].

EXAMPLE 1

Synthesis of mer-[RuCl$_3$(DMSO)$_2$(NH$_3$)]

At r.t., gaseous NH$_3$ is bubbled into a solution of mer-RuCl$_3$(DMSO)$_3$ (0.5 g) in deaerated CHCl$_3$ (15 ml). In a 5 min. period, the solution colour turns rapidly from orange to red and finally to yellow, then the precipitation of the title compound (m.p. 145° C.) occurs as yellowish microcrystals that are filtered, washed with Et$_2$O and dried.

EXAMPLE 2

Synthesis of mer-[RuCl$_3$(DMSO)$_2$(Imidazole)]

A solution of imidazole (0.25 g) in CHCl$_{13}$ is added to a stirred solution of mer-RuCl$_3$(DMSO)$_3$(0.5 g) in deaerated CHCl$_3$ (6 ml).

In a 5 min period, the solution colour changes from orange to yellow and a crystalline precipitate of the title compound (m.p. 157° C.) separates.

EXAMPLE 3

Synthesis of trans-[Ru(DMSO)($NH_3$)$Cl_4$]Na.2DMSO

At r.t., gaseous ammonia is bubbled into a stirred suspension of trans-[Ru(DMSO)$_2$$Cl_4$]Na (0.5 g) in a deaerated mixture of acetone (10 ml ) and DMSO (2 ml ). Rapidly a yellowish solution is obtained that after few minutes separates orange crystals of the title compound (m.p. 133° C.) that are filtered, washed with cold acetone and dried.

EXAMPLE 4

Synthesis of trans-[Ru(DMSO)(Imidazole)$Cl_4$]Na.2DMSO

At r.t., a solution of imidazole (0.4 g) in acetone (3 ml) is added to a stirred suspension of trans-[Ru(DMSO)$_2$$Cl_4$]Na in a deaerated mixture of acetone (8 ml) and DMSO (1.5 ml).

In a 5 rain period, a complete solution of reagents is observed; the reaction mixture colour changes from orange to yellow-orange and precipitation of the title compounds occurs as yellow-orange crystals, that are filtered, washed on filter with cold acetone and $Et_2O$ and dried (90% yield).

EXAMPLE 5

Synthesis of mer-[$RuCl_3$(TMSO)$_2$($NH$)$_3$]

At r.t., gaseous $NH_3$ is bubbled into a solution of mer-$RuCl_3$(TMSO)$_3$(0.3 g) in deaerated $CHCl_3$ (15 ml).

The colour of the solution turns very rapidly from orange to red and then to yellow (5') and the product precipitates in form of a yellowish microcrystalline precipitate, that is filtered, washed with ether and dried. (m.p. 154° C., 80% yield).

EXAMPLE 6

Using in the process of example 1 the complex mer-[$RuCl_3$(S-methyltolylsulphoxide)$_3$]the complex mer-[$RuCl_3$(S-methyltolylsulphoxide)$_2$($NH_3$)]is prepared.

EXAMPLE 7

Using in the process of example 2 a chiral amine selected in the group of S-ephedrine, S-1-phenylethylamine, R-1-phenylethylamine, the following complexes are prepared:

mer-[$RuCl_3$(DMSO)$_2$(S-ephedrine),
mer-[$RuCl_3$(DMSO)$_2$(S-phenylethylamine)],
mer-[$RuCl_3$(DMSO)$_2$(R-phenylethylamine)].

EXAMPLE 8

Using in the process of example 3 a chiral amine selected in the group of S-1-phenylethylamine, R-1-phenylethylamine, the following complexes are prepared:

trans [Ru(DMSO)(S 1 phenylethylamine)$Cl_4$]Na.2DMSO,
trans [Ru(DMSO)(R 1 phenylethylamine)$Cl_4$]Na.2DMSO.

EXAMPLE 9

Using in the process of the example 2 a N-heterocyclic ligand selected from indazole, pyridine, quinoline, isoquinoline, 1-methyl-imidazole, benzimidazole and nicotamide, the following complexes are prepared:

mer-[$RuCl_3$(DMSO)(indazole)]
mer-[$RuCl_3$(DMSO)(pyridine)]
mer-[$RuCl_3$(DMSO)(quinoline)]
mer-[$RuCl_3$(DMSO)(isoquinoline)]
mer-[$RuCl_3$(DMSO)(1-metyl-imidazole)]
mer-[$RuCl_3$(DMSO)(benzimidazole)]
mer-[$RuCl_3$(DMSO)(nicotinamide)]

EXAMPLE 10

Syntesis of trans-[Ru(DMSO)(indazole)$Cl_4$]Na.2DMSO

At r.t., 0.65 g of indazole are added to suspension of trans-[Ru(DMSO)$_2$$Cl_4$]Na in a mixture of deaerated acetone (10 ml ) and DMSO (2 ml ): after 15 min, a clear deep orange solution is formed from which orange red crystals of the title compound (m.p. 124° C.) are precipitated by dilution with diethyl ether.

Using in this procedure a N-heterocyclic ligand Selected from the group consisting of pyridine, quinoline, isoquinoline, 1-methyl-imidazole, benzimidazole and nicotamide the following complexes are prepared:

trans-[Ru(DMSO)(pyridine)$Cl_4$]Na.2DMSO
trans-[Ru(DMSO)(quinoline)$Cl_4$]Na.2DMSO
trans-[Ru(DMSO)(isoquinoline)$Cl_4$]Na.2DMSO
trans-[Ru(DMSO)(1-methyl-imidazole)$Cl_4$]Na.2DMSO
trans-[Ru(DMSO)(benzimidazole)$Cl_4$]Na.2DMSO
trans-[Ru(DMSO)(nicotinamide)$Cl_4$]Na.2DMSO

We claim:

1. Complexes of formula I:

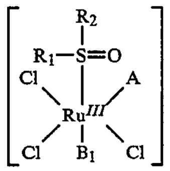

(I)

wherein $R_1$ and $R_2$, which are the same or different, are $C_1$-$C_6$ alkyl, $C_3$–$C_7$ cycloalkyl, $C_3$–$C_7$ cycloalkyl-($C_1$–$C_6$)-alkyl, phenyl, aryl-($C_1$–$C_6$)-alkyl wherein the aryl group is benzyl, phenyl, or tolyl, and each of the phenyl or aryl-($C_1$–$C_6$)-alkyl groups can be substituted by one or more ($C_1$–$C_4$) alkyl, methoxy, halogen, nitro, cyano, hydroxy, ($C_1$–$C_6$)-alkoxycarbonyl, trifluoromethyl groups or $R_1$ and $R_2$ together with the sulphur atom to which they are bound form a ring of formula

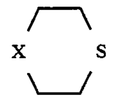

wherein X is a bond oxygen or a —$(CH_2)_m$ group;

m=1 or 2,

A is a group

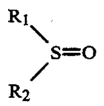

as defined above or chlorine;

$B_1$ is nitrogen ligand selected from the group consisting of ammonia, a primary, secondary, or tertiary amine or a nitrogen containing heterocyclic group selected from the group consisting of histidine, N-methyl-N-(histidyl)-amine, morpholine, piperidine, N-methyl-morpholine, N-methyl-piperidine, N-benzyl-piperidine, pyridine, imidazole, indazole, benzimidazole, 1-methyl-pyrrole, 1-benzylpyrrole, thiazole, oxazole, 1-methylimidazole, 3,5dimethylisoxazole, pyrazole, 1-methylpyrazole, 1-benzyl-pyrazole, indole, and 2-methylindole, their salts with non toxic counterions, or hydrate or solvates made with inert solvent thereof.

2. Complexes according to claim 1, wherein A is chlorine in form of salts with non-toxic counterions.

3. Complexes according to claim 1, wherein A is a group

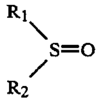

wherein $R_1$ and $R_2$ are as above defined.

4. Complexes according to claim 3, wherein both $R_1$ and $R_2$ are methyl.

5. Complexes according to claim 1, wherein $B_1$ is a primary, secondary or tertiary amine of formula NRaRbRc, wherein Ra, Rb and Rc, that can be the same or different, are hydrogen; $C_1C_6$-alkyl optionally substituted by one or more hydroxy, $C_1$–$C_4$-alkoxy, $C_1$–$C_4$-alkylthio, $C_3$–$C_7$-cycloalkyl, phenyl, phenoxy, benzyloxy, 4-histidyl, carboxy, $C_1$–$C_4$-alkoxy carbonyl groups; $C_3$–$C_7$-cycloalkyl; phenyl; the phenyl, phenoxy or benzyloxy groups being optionally substituted by one or more hydroxy or $C_1$–$C_6$ alkyl groups.

6. Complexes according to claim 5 wherein $B_1$ is $NH_3$.

7. Pharmaceutical compositions containing as an active principle a compound of claim 1, in admixture with a suitable excipient or vehicle.

8. A pharmaceutical combination comprising the complex of claim 1 and platinum complexes for contemporary, sequential or separate use in cytostatic and antitumor therapy.

9. A method of cytostatic or anti-tumor therapy comprising administering to a patient in need of such therapy a cytostatic or anti-tumor effective amount of the complex of claim 1.

10. A method of cytostatic or anti-tumor therapy comprising administering to a patient in need of such therapy a cytostatic or anti-tumor effective amount of the complex of claim 1, in combination with platinum complexes.

* * * * *

UNITED STATES PATENT AND TRADEMARK OFFICE

CERTIFICATE OF CORRECTION

PATENT NO. : 5,409,893

DATED : April 25, 1995

INVENTOR(S) : Enzo ALESSIO et al

It is certified that error appears in the above-identified patent and that said Letters Patent is hereby corrected as shown below:

On the title page, item [75], change "Sabria Pocar" to -- Sabrina Pacor --.

Signed and Sealed this

Twenty-sixth Day of September, 1995

Attest:

BRUCE LEHMAN

*Attesting Officer*

*Commissioner of Patents and Trademarks*